United States Patent [19]

Dobkin et al.

[11] Patent Number: 4,617,379

[45] Date of Patent: Oct. 14, 1986

[54] HIGH TITER CYTOMEGALOVIRUS IMMUNE SERUM GLOBULIN

[75] Inventors: Milton B. Dobkin, Lafayette; Robert E. Louie, Berkeley, both of Calif.

[73] Assignee: Miles Laboratories, Inc., Elkhart, Ind.

[21] Appl. No.: 504,105

[22] Filed: Jun. 14, 1983

[51] Int. Cl.[4] .............................................. A61K 39/00

[52] U.S. Cl. ........................................ 530/388; 424/85

[58] Field of Search ........................... 424/85, 86, 177; 260/112 R, 112 B

[56] References Cited

U.S. PATENT DOCUMENTS

| | | | |
|---|---|---|---|
| 3,903,262 | 9/1975 | Pappenhagen et al. | 424/85 |
| 4,153,683 | 5/1979 | Stephan | 424/85 |
| 4,165,370 | 8/1979 | Coval | 424/85 |
| 4,168,303 | 9/1979 | Nishida et al. | 424/85 |
| 4,174,388 | 11/1979 | McAleer et al. | 424/86 |
| 4,186,192 | 1/1980 | Lundblad et al. | 424/85 |
| 4,371,520 | 2/1983 | Uemura et al. | 424/85 |
| 4,396,608 | 8/1983 | Tenold | 424/85 X |

OTHER PUBLICATIONS

Cohn et al., J.A.C.S., vol. 69, pp. 459–475, 1946.

Zaia et al., J. Int. Dis., vol. 137, No. 5, pp. 601–604, 1978.

Lichter, Annals of the New York Academy of Sciences, vol. 162, Art. 1, pp. 43–49, 1969.

Williams, Jr., et al., Annals of The New York Academy of Sciences, vol. 94, Art. 1, pp. 77–92, 1961.

Stiehm, Pediatrics, vol. 63, No. 1, 301–319, 1979.

Graham et al., J. Immun., vol. 107, No. 6, 1618–1630, 1971.

*Primary Examiner*—Sidney Marantz

*Assistant Examiner*—Shawn P. Foley

*Attorney, Agent, or Firm*—Lester E. Johnson; James A. Giblin

[57] ABSTRACT

Normal plasma from donors who have not been vaccinated with a cytomegalovirus vaccine can be screened for higher than normal titers of naturally occurring antibody to cytomegalovirus. Those plasmas with high titers of such antibody can be pooled and fractionated to give hyperimmune serum globulin. The product may be treated to render it suitable for intravenous injection. Patients with cytomegalovirus infection or at risk to such infection, may receive the present product to raise serum titers of cytomegalovirus antibody.

10 Claims, No Drawings

HIGH TITER CYTOMEGALOVIRUS IMMUNE SERUM GLOBULIN

BACKGROUND OF THE INVENTION

1. Field of the Invention

This invention relates to and has amont its objects to a novel immune serum globulin and novel methods for its production. Particularly, the invention is concerned with an immune serum globulin having a high titer of naturally occurring antibody to cytomegalovirus (CMV). Further objects of the invention will be evident from the following description wherein parts and percentages are by weight unless otherwise specified.

2. Description of the Prior Art

Hyperimmune serum globulins, i.e., immune serum globulins having high titers of a particular antibody, are thereapeutically useful in treating patients deficient or in need of that particular antibody. For example, tetanus hyperimmune globulin is useful in treating tetanus, and rabies hyperimmune globulin, rabies. It is well known that hyperimmune serum globulins can be produced from plasma or serum obtained from selected donors who have significantly higher titers for a specific antibody than is normally found in the average population. These donors have either been recently immunized with a particular vaccine (U.S. Pat. No. 4,174,388) or else they have recently recovered from an infection or disease [Stiehm, *Pediatrics,* Vol. 63, No. 1, 301–319 (1979)].

Although clinical disease from cytomegalovirus (CMV) is not common among the general population, it is encountered very frequently in certain susceptible groups of patients. Immumosuppressed organ transplant and cancer patients have been identified as having an unusually high risk of acquiring severe, and sometimes fatal, CMV infection.

Zaia et al in *The Journal of Infectious Diseases,* Vol. 137, No. 5, 601–604 (1978) disclosed a practical method for preparation of Varicella-Zoster (VZ) Immune Globulin. Outdated blood was screened for complement-fixing antibody to VZ virus. About 15% of the plasma units has a complement-fixation titer equal to or greater than 1:16, with about 7.5% greater than or equal to 1:32.

SUMMARY OF THE INVENTION

We have found that normal fresh plasma from donors who have not been vaccinated with a CMV vaccine can be screened for higher than normal titers of antibody to CMV. Those plasmas with antibody titers greater than about 1:60,000, determined by means of an enzyme-linked immunosorbent assay (ELISA), can be pooled and then fractionated to give a CMV hyperimmune serum globulin. This result is surprising because it is unexpected that plasma from normal, unvaccinated donors would have a titer of antibody to CMV high enough to yield a CMV hyperimmune globulin which would be effective in treating CMV infections.

One obvious advantage of the invention is that normal donors need not be given a CMV vaccine. Consequently, the risks inherent in such a practice are avoided. Another advantage of the invention is that the hyperimmune globulin given intravenously makes antibodies to CMV immediately available. Another advantage resides in avoiding patient discomfort associated with intramuscular administration. Other advantages are elimination of a delay of several days for CMV antibodies to reach a peak in the circulation, and elimination of local degradation. Furthermore, less product needs to be administered intravenously in order to achieve the same level of antibody obtained with an intramuscularly administered product or higher doses can be administered intravenously to provide higher titers which would otherwise be impossible to obtain by intramuscular administration.

DESCRIPTION OF THE PREFERRED EMBODIMENTS

These and other advantages of the present invention may be obtained in the following manner.

Normal plasma from a donor is tested for naturally occurring antibody to CMV employing an ELISA or other equally sensitive screening method at equivalent titer. To be effective the plasma from such donors should have a titer of antibody to the CMV equal to or greater than about 1:60,000. We have found that about 4–8% of plasma donors in fact have such a titer. These donations may be selected from a routine donor collection by random screening. Generally, the hyperimmune serum globulin of the invention has a titer of antibody to CMV of about 1:150,000–1:1,225,000, preferably about 1:450,000–1:615,000.

The method of screening the plasma, i.e. the ELISA method, is essentially as described by Engvall and Perlmann, *J. Immunol.,* 109, 129–135 (1972), Engvall et al, *Biochemica Et Biophysica Acta,* 251 (1971) 427–434, Engvall et al, *Immunochemistry,* 8, 871–874 (1971), which are all incorporated herein by reference. The assay is a simple method for the quantitative determination of antibodies. Microtiter plates coated with antigen are incubated with antiserum followed by an enzyme-labeled preparation of anti-globulin. The enzyme-labeled anti-globulin remaining in the wells after washing and quantitated by addition of a chromogenic substrate, provides a measure of the amount of specific antibodies in serum.

Plasma having a sufficiently high titer of antibody is pooled and fractionated to obtain an immune serum globulin. To this end one may employ any method for obtaining an intravenously injectable immune serum globulin from pooled plasma. For example, one may employ the Cohn fractionation method (referenced hereinabove, which references are incorporated herein by reference thereto) an ammonium sulphate fractionation, polyethylene glycol precipitation or the like. The aforementioned immune serum globulin comprises IgG, usually at least 90% IgG monomer. The material generally also contains other globulins such as IgA, IgM, and the like.

These high titer sera or plasmas are pooled and subjected to the Cohn fractionation method to produce Fraction II [Cohn et al, *J. Am. Chem. Soc.,* 68, 459 (1946) and Oncley, et al, ibid., 71, 541 (1949)].

As mentioned above, the CMV hyperimmune globulin may be intramuscularly or intravenously injectable. The latter material is preferred and may be prepared, for example, according to the method of Tenold, "Intravenously Injectable Immune Serum Globulin", U.S. Ser. No. 295,916, filed Aug. 24, 1981 and/or U.S. Pat. No. 3,903,262 (which are incorporated herein by reference) or any of the methods referred to in the above-identified U.S. patent.

The modified immune serum globulin of U.S. Pat. No. 3,903,262 is adapted for intravenous injection and consists of intact immune serum globulin chains having partly intact interchain disulfide linkages. Each cleaved disulfide linkage is replaced by a pair of alkylated mercapto groups, the cleaved chains remaining united by non-covalent association so that the apparent molecular weight of the modified serum globulin in non-dissociating solvents is essentially the same as unmodified immune serum globulin. The above material is produced by reducing, in a mildly alkaline aqueous solution, immune serum globulin with dithiothreitol or dithioerythritol, alkylating the thus-reduced interchain disulfide groups, and separating the thus-modified globulin from the non-proteinaceous reaction products.

The hyperimmune globulin preparation of this invention can also include maltose as a stabilizer in accordance with the teaching of U.S. Pat. No. 4,186,192. Accordingly, the instant preparation may contain about 1-20% of maltose on a weight to volume basis.

The hyperimmune products of the invention may be manufactured as pharmaceutical preparations, usually aqueous solutions of the hyperimmune serum globulin which may be used for prophylactic and therapeutic purposes.

The pharmaceutical preparation intended for therapeutic use should allow delivery of a therapeutic amount of hyperimmune serum globulin, i.e., that amount necessary for preventive or curative health measures.

EXAMPLES

The invention is demonstrated further by the following illustrative examples.

Assay Method

The ELISA method was essentially the same as that described by Engvall and Perlmann, ibid., and used by Carlsson et al. *Inf. Imm.*, 6 (5) 703-708 (1972) for titration of anti Salmonella immunoglobulins. The method has been previously adapted for microtiter plates Voller et al. *Manual of Clinical Immunology*, 1976, 506-512, where visual endpoints can be determined with good sensitivity, Poxton, *J. Clin. Path.*, 32, 294-295 (1975), Voller et al, supra.

Round bottomed wells in polystyrene microtiter plates were sensitized by addition of 0.1 ml of CMV antigen in carbonate-bicarbonate buffer, pH 9.5, and incubated at 4° C. for approximately 18 hours. CMV antigen is obtained by infecting MCR5 cells with CMV (strain AD 169) and harvesting the viral antigen according to the procedure described by Forghani et al, "Antibody Assays for Varicella-Zoster Virus:Comparison of Enzyme Neutralization, Immune Adherence, Hemagglutination, and Complement Fixation", in J. Clin. Microbiol. 8:5, 545-552 (1978). Plates were washed once with phosphate buffered saline (PBS) containing 0.05% Tween 20 and 0.2% sodium azide (PBSTA). Five percent Bovine serum albumin (BSA), 0.1 ml was added to each well. The plates were further incubated 4-5 hours at room temperature, followed by one wash. The plates were shaken dry after the final wash. Dilutions of antisera were added to each well (0.1 ml) and incubated overnight at room temperature. Wells were washed three times as before and 0.1 ml of goat anti-human IgG conjugated to alkaline phosphatase (Miles Laboratories, Inc.) was added to each well and incubated 2 hours at room temperature. After again washing the wells, 0.1 ml of a 1.0% (w/v) solution of enzyme substrate, p-nitrophenyl phosphate, (Sigma Chemical Co.) in 10% diethanolamine buffer, pH 8.0, with 0.02% sodium azide and 1 mM Mg $Cl_2$ was added and incubated for 30 minutes, at room temperature. The reaction was stopped by the addition of 0.05 ml of 3N NaOH to each well. The absorbance was read at 405 nm with a Dynatech model 580 micro ELISA reader. The endpoint was taken to be the highest dilution with an absorbance ≧0.010.

Example 1

Plasma donations obtained from donors were screened for high titer of antibody to cytomegalovirus (CMV) using the ELISA method. Plasma with a CMV antibody titer of 1:60,000 or greater were pooled and fractionated to give an intravenously injectable immune serum globulin (IGIV).

The method of U.S. Pat. No. 3,903,262 was followed. Briefly, Cohn Fraction II paste was prepared from the pooled plasma (400 liters) and was suspended in an aqueous sodium chloride solution, which was warmed and mixed with a solution of dithiothreitol. Iodoacetamide was added to the mixture. Next, the mixture was diafiltered to remove residual reagents. After pH adjustment, the material is sterile filtered.

The so-prepared IGIV exhibited a titer of antibody to cytomegalovirus of about 1:448,352 as measured by ELISA.

Example 2

Prior to clinical trials of any biological product, its biological activity is usually assessed first in an animal model system. In the case of human CMV, however, no such model exists, and for this reason a study was undertaken to evaluate the biological activity of CMV-IGIV by means of a virus neutralization test.

The ability of CMV to infect human cells in culture, resulting in visible cytopathology, permitted evaluation of the neutralizing antibody content of CMV-IGIV by means of a semi-quantitative assay, the plaque reduction neutralization test. The procedure used for these tests was essentially the one reported by Schmidt et al; *J. Clin. Microbiol.* 4:61, 1976, with slight modifications. The important differences are:

1. MRC-5 cells were used both for the propagation of virus stocks and for the performance of the test.
2. Trypsin was included in the overlay medium, which resulted in increased plaque counts.

The basic methodology is similar to plaque assays employed with other viruses, differing primarily in the incorporation of complement (guinea pig serum), which has been shown to enhance neutralizing antibody titers.

IGIV prepared from non-selected plasma was used as a control.

Using the plasma reduction neutralization test, a comparison was made of the neutralizing antibody titers of matched plasma pools and final product for both CMV-IGIV and control IGIV. Table 1 shows a summary of the results of these tests; the antibody titers are expressed as 50% plaque reduction endpoints, determined from regression lines plotted from the probit of percent plaque reduction versus the log of the reciprocal of the antibody dilutions.

TABLE 1

| Sample Identification | Product Type | Neutralizing Antibody Titer | ELISA Titer |
|---|---|---|---|
| Selected Plasma Pool | Plasma | 1:88 | 1:96,764 |
| Hyperimmune Globulin | CMV-IGIV | 1:119 | 1:448,363 |
| Unselected Plasma | Plasma | 1:28 | 1:11,085 |

TABLE 1-continued

| Sample Identification | Product Type | Neutralizing Antibody Titer | ELISA Titer |
|---|---|---|---|
| Pool No. 1 | | | |
| Immune Globulin No. 1 | IGIV | 1:32 | Not Done |
| Unselected Plasma Pool No. 2 | Plasma | 1:41 | 1:15,677 |
| Immune Globulin No. 2 | IGIV | 1:21 | 1:51,200 |
| Unselected Plasma Pool No. 3 | Plasma | 1:14 | 1:14,311 |
| Immune Globulin No. 3 | IGIV | 1:61 | 1:76,800 |
| Unselected Plasma Pool No. 4 | Plasma | 1:17 | 1:12,800 |
| Immune Globulin No. 4 | IGIV | 1:29 | 1:64,000 |

The geometric mean neutralizing antibody titer of the unselected plasma pools is 1:23.
The geometric mean neutralizing antibody titer of the IGIV lots is 1:33.
The geometric mean ELISA titer of the unselected plasma pools is 1:13,357.
The geometric mean ELISA titer of the IGIV PR lots is 1:63,135.

What is claimed is:

1. A method for preparing a human immune serum globulin having a titer of antibody to cytomegalovirus in the range of about 1:150,000–1:1,225,000 determined by an enzyme-linked immunosorbent assay which comprises (a) screening plasma from donors who have not been vaccinated with a cytomegalovirus vaccine for a titer of antibody to cytomegalovirus of at least about 1:60,000 determined by an enzyme-linked immunosorbent assay, (b) pooling plasma donations of said titer of antibody to cytomegalovirus, and (c) preparing an immune serum globulin from said pooled plasma.

2. The method of claim 1 which further includes the step of rendering the human immune serum globulin of step c intravenously injectable.

3. The method of claim 1 wherein the immune serum globulin is produced by the Cohn fractionation method.

4. The method of claim 1 wherein the human immune serum globulin is reduced and alkylated to render it intravenously injectable.

5. The method of claim 1 wherein the human immune serum globulin is produced by forming a solution of immune serum globulin and adjusting the pH and ionic strength to maintain the monomer content and the actual and latent anticomplement activity of the immune serum globulin such that the composition is intravenously injectable.

6. The method of claim 1 wherein the human immune serum globulin comprises IgG.

7. A human immune serum globulin produced by the method of claim 14 having a titer of antibody to cytomegalovirus of about 1:150,000–1:1,225,000 determined by an enzyme-linked immunosorbent assay, said immune serum globulin being effective to treat cytomegalovirus infections.

8. A pharmaceutical preparation comprising an aqueous solution of the human immune serum globulin of claim 7.

9. The preparation of claim 8 which further includes maltose.

10. The human immune serum globulin of claim 7 which is intravenously injectable.

* * * * *

UNITED STATES PATENT AND TRADEMARK OFFICE
CERTIFICATE OF CORRECTION

PATENT NO. : 4,617,379
DATED : October 14, 1986
INVENTOR(S) : MILTON B. DOBKIN and ROBERT E. LOUIE It is certified that error appears in the above-identified patent and that said Letters Patent are hereby corrected as shown below:

In claim 7, line 2, "claim 14" should be --claim 1--.

Signed and Sealed this

Sixth Day of January, 1987

*Attest:*

DONALD J. QUIGG

*Attesting Officer*

*Commissioner of Patents and Trademarks*